United States Patent [19]

McKenzie

[11] Patent Number: 5,429,817
[45] Date of Patent: Jul. 4, 1995

[54] INSECT REPELLENT FOR FRUITS, VEGETABLES AND PLANTS

[76] Inventor: John McKenzie, 1777 Camino Sierra, Bakersfield, Calif. 93306

[21] Appl. No.: 148,960

[22] Filed: Nov. 8, 1993

[51] Int. Cl.$^6$ .............................................. A61K 35/78
[52] U.S. Cl. ...................... 424/195.1; 424/DIG. 10; 514/919
[58] Field of Search ................ 424/195.1, DIG. 10; 514/919

[56] References Cited

U.S. PATENT DOCUMENTS

| | | | |
|---|---|---|---|
| 4,022,923 | 5/1977 | Berger | 426/638 |
| 4,377,600 | 3/1983 | Morinaga | 426/424 |
| 4,455,304 | 6/1984 | Yaralian | 424/195.1 |
| 4,876,090 | 10/1989 | Weisler | 424/195.1 |

Primary Examiner—Douglas W. Robinson
Assistant Examiner—Howard C. Lee
Attorney, Agent, or Firm—Francis X. LoJacono

[57] ABSTRACT

A nontoxic insect repellent that is adapted to be sprayed on fruits, vegetables and plants of all types, wherein the liquid insect repellent consists of two basic ingredients comprising filtered water and garlic juice which is extracted from a given batch of fresh frozen garlic puree. The garlic juice and filtered water are mixed under controlled temperatures during which the mixture is filtered to provide a blended liquid in a colloidal suspension within a refrigerated holding tank wherein the liquid is constantly recirculating through a refrigeration system for a selected time period under an established regulated temperature, thereby preventing settling and disruption of enzyme activity so that a required pH factor is established.

6 Claims, No Drawings

INSECT REPELLENT FOR FRUITS, VEGETABLES AND PLANTS

BACKGROUND OF THE INVENTION

Field of The Invention

This invention relates to an insect repellent and more particularly to a process for producing a nontoxic insect repellent that is adapted to be applied to fruits, vegetables and plants of all types, wherein the liquid insect repellent consists of the basic ingredients of water and a garlic juice that is mixed under various steps during which the mixture is filtered to provide a liquid in a colloid suspension within a storage or holding tank during which the liquid is constantly recirculating through a refrigeration system to establish a regulated temperature and prevent settling and disruption of enzyme activity.

The use of water as a carrier for garlic is well known as indicated in Chem. Abst. 106:456978 and has been used for various applications, such as the example as disclosed in U.S. Pat. No. 4,876,090 to Richard Weisler. This particular patent provides protection for domesticated animals against fleas, ticks and other blood feeding pests. The composition of this invention consists of two essential ingredients: Vitamin $B_1$ and allyl sulfide (garlic oil) dissolved in a soybean oil base.

A variety of insecticides comprising both synthetic and/or natural chemicals have been developed over the years for controlling insects that attack various types of fruits and vegetables as well as the foliage of trees and shrubbery. However, many of these insecticides have been found to be toxic and many have been restricted in their use or have been prohibited altogether, particularly when applied to edible fruits and vegetables.

Accordingly, there is a great need for a simple insect repellent that can be freely applied to all kinds of edible produce without the use of cancer causing chemicals. Because of increasing public awareness of the potential hazard from long term exposure to such toxic agents, the use of natural products for control of insect infestation of farm produce is receiving greater consumer acceptance.

As is thus evident, there is a great need for a safe and effective insect repellent that can be applied to fruits and vegetables and that will not cause a harmful reaction in humans, and more particularly to an insecticide that will allow for the consumption of produce on a regular basis without fear.

OBJECTS AND ADVANTAGES OF THE INVENTION

It is an important object of the present invention to provide a nontoxic insect repellent that allows farm-products to be treated with the repellent without harmful consumer side effects as would be the case with most known chemically activated repellents.

Another object of the present invention is to provide a natural nontoxic insect repellent liquid that can be readily applied to fruits and vegetables as well as plants and trees, the insect repellent being basically formed from garlic and water, wherein the process or method of making and producing the repellent leaves no residual garlic odor and/or garlic taste on the fruits and vegetables.

Still another object of the present invention is to provide a nontoxic insect repellent material wherein the fermentation aspect of the process isolates the odor-causing molecules and promotes quick oxidation of these molecules.

A further object of the invention is to provide an insect repellent of this character wherein the temperature control, fermentation time and lack of any heat in this process are the critical elements in creating a product that is cost-effective for wide-scale applications in agriculture.

A still further object of the present invention is to provide a new process for producing a nontoxic insect repellent which basically consists of water and crushed garlic in the form of a puree, whereby the final product formed by this new process is a garlic extract concentrate that defines an edible nontoxic liquid insect repellent that results in no residual after effects to either the food product to which it is applied to or to those who consume such produce treated by the repellent composition due to the new and unique steps that are required in the manufacture the end product.

DESCRIPTION OF THE INVENTION INCLUDING THE PREFERRED EMBODIMENT

The present invention relates to a process for manufacturing a nontoxic insect repellent which basically starts with obtaining food-grade garlic cloves that are machine-cleaned of all husks and stems, followed by crushing and the immediate fast-freezing of the crushed material. The crushing of the clean garlic cloves creates a garlic puree that is stored frozen in single five (5) gallon containers. From this stage a garlic extract is created that defines a final garlic product made for general production in approximately two hundred and seventy-five gallon batches in a blending machine. However, it should be understood that the garlic puree need not be frozen if the garlic cloves are freshly crushed just prior to being used in the process.

The following is a more detailed description of the typical steps employed to create a final product that is a nontoxic insect repellent liquid consisting of the combination of the two basic ingredients which are garlic extract and water. When uniquely mixed and processed the garlic extract and water mixture provides an end product that defines a nontoxic insect repellent which is readily applied by the periodic spraying of fruits, vegetables, plants and trees having all types of foliage that require protection from insects. Further, during the fermentation aspect of the process the odor-causing molecules are apparently isolated, causing quick oxidation of these molecules. Thus, it is important to note that no residual garlic and/or garlic taste is transferred to the fruits and vegetables.

An appropriate number of five gallon containers of frozen crushed garlic puree are allowed to thaw for approximately forty-eight hours in a refrigerator set at 41° F. When a particular container has fully thawed, it is stirred and a sample is drawn to determine moisture content through vacuum oven. The pulp component of the garlic puree is not a factor in the manufacture of the end product, but dissolved solids such as organic selenium and germanium, and soluble solids such as iron, are important components of the product. EPA requires a concentrate that is ten percent (10%) garlic and ninety (90%) water, plus or minus one percent. This means that two hundred seventy-five gallons of concentrate must have approximately 27.5 gallons of garlic liquid added.

After the above steps have been taken the a proper amount of garlic puree is added to a retainer basket of the batch tank of the blending machine to obtain the correct blending ratio. The proper amount is determined by the results of the above-noted moisture content test. For example, if the moisture content of the preprocessed garlic puree is 50% then 55 gallons of this puree, with 50% pulp removed, will be required (assuming a 50% moisture content) and would be blended with 220 gallons of water at between 79° to 84° F., preferably filtered water. Before water is deposited into the batch tank it goes through two stages. First, the water is passed through a 5-micron particle filter, and second through an activated carbon filter to reduce chlorine and other undesirable contaminating elements. The puree at this time occupies approximately half of the volume of the retainer basket which is adapted to rotate on a main shaft of the blending machine, whereby the puree tumbles inside the retainer basket as the shaft turns. Because the basket is located near the bottom of the batch tank which is filled nearly to the top, the resultant fluid pressure facilitates a "washing out" action of the liquid component (liquid concentrate) of the garlic puree. The retainer basket preferably operates at 30 revolutions per minute (RPM) during blending.

During the blending stage of the process the temperature and pH of the material must be monitored and controlled. The temperature of the liquid should range between 38° and 45° F. during the blending step of the process, with the ideal temperature of 41° F. being preferred. Incoming water temperature is monitored, and if it is not within the required range, a bypass valve is activated for precooling the water before it goes into the blending machine. Both the precooling of water before use and the continuous cooling of the liquid mixture in the tank during processing are accomplished by recirculating the liquid through copper coils that extend within a refrigeration system. The minimum running time for blending is 20 minutes per batch and the maximum time is 60 minutes. No further "washing-out" of the liquid garlic concentrate of the garlic puree will occur by running the blending machine for more than 60 minutes. The preferable operating time for the best results is approximately 40 minutes. Accordingly, when the tumbling cycle is completed, the liquid concentrate in the batch tank is then filtered through a three-stage, automatic, "wash-down" type filter system to eliminate particles over 20 microns in size, and pumped into a holding tank. As the blending machine/batch tank is emptied, the shaft RPM is increased to 500 to centrifuge excess liquid from the pulp that remains from the original garlic puree. Pulp is then removed from the blending machine basket, and residual liquid in the pulp may be pressed out and added to the holding tank. However, this is an optional step and is not always required. This particular tank will be allocated for that specific batch number, with a separate holding tank for each batch.

The blended liquid in the holding tank is a colloid suspension that is typically a clear or pale amber color. Thus, in order to prevent settling and disruption of enzyme activity, the liquid is constantly recirculated through the refrigeration unit described above and, if necessary, cooled to maintain the optimum 41° F. temperature. However, during the recirculation of the blended liquid, the suspended solids, which consists primarily of pulp, are sometimes required to be removed. That is, if the pulp is highly sulphurous and when in suspension and when combined with oxygen, it produces suphuric acid which will spot and/or bum the plants upon which the product is sprayed. To prevent this the product is first filtered at high pressure through two 15 inch diameter cylindrical filter canisters, each containing approximately 60 inches of garnet filter media, ranging in size from 400 microns to 20 microns. This is followed by the final filtration of the liquid through three sequentially smaller canisters containing polypropylene filter cartridges of 20, 5 and 1 micron size. This filtration ensures removal of all pulp without affecting the oil component of the product, since garnet and polypropylene filter media do not trap nor retain oils. Clarity of the product is the first indicator that it is ready for shipment.

The initial pH of each batch immediately after blending may vary somewhat depending on the balance of enzymes and amino acids, but will typically average 5.0 immediately after blending. As a foliar treatment, the systemic action of the product is not achieved fully until a pH of 3.2 is achieved. This pH is reached naturally through continued enzyme and amino acid activity. The enzyme/amino acid activity is regulated mainly by maintaining the water temperature of the batch between 38° and 45° F., with 41° F. once again being the optimum processing. When the batch is maintained in the holding tank at exactly 41° F. and continuously recirculated, the elapsed time required for the pH to drop to 3.2 through natural fermentation will typically be approximately four days, or 96 hours. Due to the wide range of variables which is always present in the realm of organic chemistry, a few individual batches achieve the required 3.2 immediately after blending, and other batches may require up to seven days to reach the correct pH.

When the 275 gallons of product have completed all the steps of the manufacturing process, the insect repellent is ready for bottling and packaging, and it is no longer essential to keep cooling the liquid once the proper pH has been achieved as the product has demonstrated a shelf life of three years without refrigeration.

EXAMPLE I

The following is an example of how to obtain two hundred and seventy-five gallons of finished product of the nontoxic insect repellent that consists of ten percent (10%) garlic solution to ninety percent (90%) aqueous solution, plus or minus one percent (1%), that is, one (1) part garlic concentrate to nine (9) parts water. A sufficient amount of cleaned garlic cloves are crushed as a garlic puree and is immediately frozen in appropriate containers, generally five (5) gallon containers, of which 6 to 7 containers are generally required for a two hundred and seventy-five gallon batch. Since the number of containers to be used are contingent on the moisture content of the puree in these containers they are taken from a given batch of frozen garlic puree and thawed for approximately 48 hours in a refrigerator set at a temperature of 41° F. When a particular container has thawed at this set temperature, it is stirred, and a sample is drawn to determine moisture content through a suitable vacuum-oven process. Each two hundred and seventy-five gallons of finished product must have approximately 27.5 gallons of garlic liquid. The results of the moisture content test determine exactly how much puree is to be added to a blending machine to provide the ratio of one (1) part concentrated garlic juice to ten (10) parts water.

Prior to adding water to the blending machine, chlorine and other contaminants are removed in two stages, first by passing the water through a 5-micron particle filter, and second through an activated carbon filter. The filtered water is added to the blending machine along with the garlic puree, at which time the liquid components of the garlic puree are washed out by placing the garlic puree in a retainer basket which is mounted and rotated in the blending machine at 30 revolutions per minute (RPM) during the blending process which takes approximately forty (40) minutes. The temperature of the liquid is maintained at a constant 41° F. during the processing by means of recirculating the liquid through a refrigerated cooling system. When the blending and tumbling cycle is completed the blended liquid in the batch tank is then filtered through an automatic "wash-down" type filter system to eliminate particles over 20 microns in size. It is then transferred to a temperature controlled holding tank, which is constantly recirculated through the refrigeration system of the holding tank, wherein the liquid is maintained at 41° F. At this time the colloidal liquid is passed through a filtration system which removes all remaining plup. The constant circulation also prevents settling and provides disruption of enzyme and amino acid activity so as to provide the proper pH reading of 3.2. A systemic action of the product is achieved for foliar treatment when the pH 3.2 reading is present.

When the process of the product is completed it consists of a nontoxic, systemic, insect repellent that can be readily applied by various methods or means such as spraying the liquid on vegetables, fruits and plants or the foliage of the plants. The liquid is absorbed into the tissues of the vegetables, fruits and plants without affecting their structure, that is, the skin and meat thereof. Moreover, there is no residual garlic odor and/or garlic taste.

To provide the necessary protection throughout the growth of plants and/or produce they must be sprayed at least twice before harvesting. More specifically, the insect repellent should be applied, such as spraying, when the plant begins to grow leaves and 10 days prior to harvesting the produce of the plant or tree. However, their are some exceptions such as cabbage and other similar produce which are sprayed when the heads are being formed and again between 14 to 17 days before harvesting.

It should be noted that the disclosure as presented herein is not intended to limit the present invention to the specific embodiments described above. For example, if the pH reading of 3.2 is not achieved at the completion of the process it would be necessary to reach the proper pH reading through continued natural fermentation by means of enzyme and amino acid activity which is provided by the continuous recirculation of the liquid at 41° F. for an elapsed time of 96 to 168 hours.

Further, as the batch tank is emptied the shaft therein can be rotated at 500 RPM to establish a centrifugal action so as to extract any excess liquid from the remaining pulp of the original garlic puree, or the pulp can be removed from the blending tank so that the residual liquid in the pulp can be pressed out by a suitable means and added to the holding tank. Each holding tank is allocated with a specific batch number, with a separate holding tank for each batch.

EXAMPLE II

This example includes Example I with the following step of filtering the suspended solids during the recirculation of the the blended liquid, which consists primarily of pulp that is first filtered at high pressure through two 15 inch diameter, cylindrical, filter canisters, each containing approximately 60 inches of garnet filter media, ranging in size from 400 microns to 20 microns. This is followed by the final filtration of the liquid through three sequentially smaller canisters containing polypropylene filter cartridges of 20, 5 and 1 micron size. This filtration ensures removal of all plup without affecting the oil component of the product, since garnet and polypropylene filter media do not trap nor retain oils.

Accordingly, it should be recognized that these and other like changes may be made in the composition and process specifically described herein without departing from the scope and teachings of the instant invention, and it is intended to encompass all other embodiments, alternatives and modifications consistent with the present invention.

What I claim is:

1. A process for producing a nontoxic, systemic, insect repellent containing garlic and water adapted for use with fruits, vegetables and plants comprising the steps of:
   blending 1 part of liquid concentrate garlic puree with 9 parts water in a refrigerated blending machine at a temperature of between 38° and 45° F. for between 20 to 60 minutes;
   refrigerating the blended liquid in a holding tank at a temperature of between 38° and 45° F. while maintaining the blended liquid as a colloidal suspension in said holding tank by recirculation to prevent settling and disruption of enzyme activity, thereby allowing the blended liquid to reach a pH of about 3.2 through fermentation; and,
   filtering the blended liquid from the suspended solids to extract and recover a liquid garlic concentrate therefrom.

2. The process as recited in claim 1, further including the step of setting the temperature of the blending machine and the holding tank at 41° F.

3. The process as recited in claim 1, further including the step of:
   maintaining the blended liquid in colloidal suspension in said holding tank by recirculating said blended liquid through refrigerating coils of the refrigerated holding tank so as to prevent settling and disruption of enzyme activity to allow the blended liquid to reach a pH of about 3.2 through fermentation.

4. The process as recited in claim 3, further including the step of filtering the water prior to the water being added to the blending machine.

5. The process as recited in claim 4, wherein the step of filtering the water prior to the water being added to the blending machine further includes first passing the water through a 5-micron particle filter, and through an activated carbon filter to reduce chlorine and other undesirable contamination elements.

6. The process as recited in claim 5, wherein the step of filtering the blended liquid from the suspended solids further includes the steps of filtering the blended liquid at a high pressure through at least one filter unit containing approximately 60 inches of garnet filter media, ranging in size from 400 microns to 20 microns followed by filtering the liquid through three sequential filters containing polypropylene filter cartridges of 20, 5 and 1 micron size.

* * * * *